United States Patent [19]

Holick

[11] Patent Number: 5,612,317
[45] Date of Patent: Mar. 18, 1997

[54] METHOD FOR DELIVERING ESTROGEN

[76] Inventor: Michael F. Holick, 31 Bishop La., Sudbury, Mass. 01776

[21] Appl. No.: 285,438

[22] Filed: Aug. 4, 1994

[51] Int. Cl.$^6$ .................................................. A61K 31/705
[52] U.S. Cl. ................................ 514/26; 536/5; 552/502
[58] Field of Search .............................. 514/26; 536/5; 552/502

[56] References Cited

U.S. PATENT DOCUMENTS

| | | | |
|---|---|---|---|
| 4,078,060 | 3/1978 | Benson et al. | 424/242 |
| 4,096,254 | 6/1978 | Benson et al. | 424/242 |
| 4,225,596 | 9/1980 | DeLuca | 424/236 |
| 4,410,515 | 10/1983 | Holick et al. | 424/180 |
| 4,521,410 | 6/1985 | Holick et al. | 514/26 |
| 5,183,814 | 2/1993 | Dukes | 514/171 |

OTHER PUBLICATIONS

Conrow & Bernstein, "Steroid Conjugates. VI. An Improved Koenigs–Knorr Synthesis of Aryl Glucuronides Using Cadmium Carbonate, a New and Effective Catalyst," *J. Org. Chem.* 36:863–870 (Apr. 9, 1971).

Fujimoto et al., "Characterization of 17β–estradiol 3–(β–D–glucopyranoside) and 17–(α–D–glucopyransoside) as the metabolites of 17β–estradiol in the cultured ovaries of the silkworm, *Bombyx mori*, " *Experientia* 42:567–568 (1986).

Hobkirk et al., "Metabolism of Intravenously Administered 17β–Estradiol–6,7–H–3–glucoside–C in Normal Women," *J. Clin. Endocrinol.* 32:476–480 (Apr. 1971).

Williamson et al., "Isolation of 17α–Estradiol 17β–D–Glucopyranoside from Rabbit Urine, and Its Synthesis and Characterization," *Biochemistry* 8:4299–4304 (Nov. 1969).

Williamson et al., "Metabolism of Intravenously Administered 17α–[6,7–H]Estradiol–17–Glucoside in Normal Women," *Canadian J. Biochem.* 50:958–962 (1972).

Rae et al. *Clinica Chimica Acta*, vol. 176, pp. 71–82, (1988).

Tanouye, *The Wall Street Journal*, 15 Jun. 95, pp. A1 and A8.

*Goodman & Gilman's The Pharmaceutical Basis of Therapeutics*, (Eighth Edition), Pergamon Press, pp. 1391, 1394–1395, (1990).

*Primary Examiner*—John Kight
*Assistant Examiner*—Howard C. Lee
*Attorney, Agent, or Firm*—Sterne, Kessler, Goldstein & Fox, P.L.L.C.

[57] ABSTRACT

The present invention relates to methods for the treatment or prevention of osteoporosis and the alleviation of the symptoms of menopause by the administration of an estrogen glycoside or estrogen orthoester glycoside.

10 Claims, 4 Drawing Sheets

METHOD FOR DELIVERING ESTROGEN

FIELD OF THE INVENTION

The invention is in the field of Medicinal Chemistry.

BACKGROUND OF THE INVENTION

Menopause is defined as the final episode of menstrual bleeding in women. The term is also used colloquially to refer to the period of time encompassing the transitional period between the reproductive years up to and beyond the final episode of menstrual bleeding. For the purposes of this invention, reference to menopause will encompass this transitional period. Menopause is the result of the cessation of follicular development, which leads to a drop in the production of estradiol and other hormones. While 60% of estrogen formed in pre-menopausal women is in the form of estradiol, most of which is produced in the ovaries of ovulating women, post-menopausal ovaries produce a minimal amount of estrogen, with extraglandular tissues providing the majority of post-menopausal estrogen synthesis.

Symptoms associated with menopause include vasomotor instability (hot flashes), a decrease in breast size, atrophy of the urogenital epithelium and skin, and osteoporosis, a disease which is characterized by a marked loss of bone mass. Hot flashes may be accompanied by nervousness, anxiety, irritability and depression. Osteoporosis and the decrease in size of the female reproductive tract and breasts have been closely correlated to low levels of estrogen, while the pathology of hot flashes, though less well understood, may also be related to the decrease in estrogen production accompanying menopause.

The significant loss of bone mass which occurs at the time of menopause ultimately gives rise to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally the disease, which is often accompanied by bone pain and decreased physical activity, is diagnosed by one or two vertebral crush fractures with X-ray evidence of diminished bone mass. It is known that this disease is accompanied by diminished ability to absorb calcium, decreased levels of sex hormones, especially estrogen and androgens, and a negative calcium balance.

Methods for treating the disease have varied considerably but to date no really satisfactory treatment is yet being practiced. For example, calcium supplementation by itself has not been successful in preventing or curing the disease. Other treatments, for which variable results have again been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered.

Estrogen therapy is the most commonly used treatment of menopausal symptoms. Estrogen therapy ameliorates symptoms including hot flashes and atrophy of the urogenital epithelium and skin, and has positive effects on the incidence of osteoporosis.

Premarin is the most widely prescribed estrogen that is used for the treatment of postmenopausal symptoms, including osteoporosis, in the United States. Premarin is obtained from pregnant mares' urine, and contains the sodium salts of water-soluble estrogen sulphates as well as a variety of estrogen derivatives. One of the reasons that Premarin is so popular is because of concern that unconjugated estradiol, when given orally, has a first pass effect on the liver. This effect can have potentially serious consequences including the increase of blood clotting factors which can increase the user's risk of developing blood clots.

U.S. Pat. No. 4,225,596 discloses methods for treating or preventing metabolic bone disease characterized by the loss of bone mass by administering at least one compound having the formulae (I) and (II):

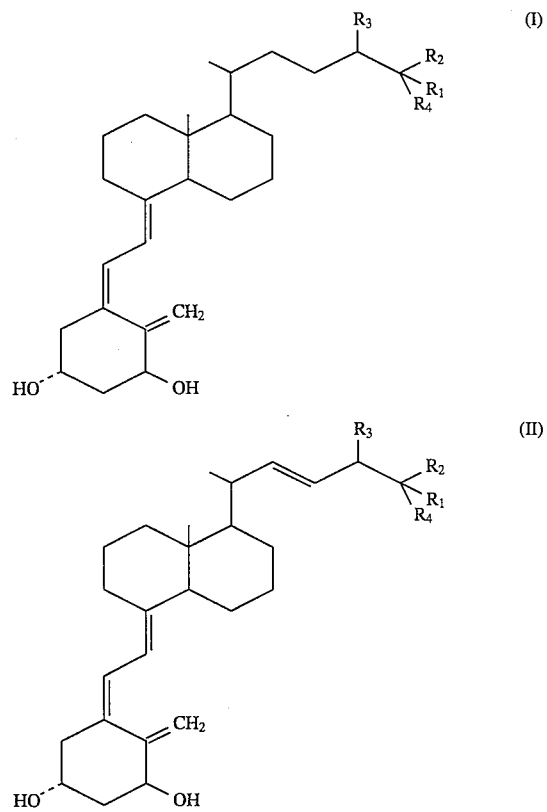

where $R_1$, $R_2$ and $R_4$ are each selected from the group consisting of hydrogen, hydroxyl, lower alkyl, acyl and O-alkyl and $R_3$ is selected from the group consisting of hydrogen, hydroxyl, keto, lower alkyl, acyl and O-alkyl.

U.S. Pat. No. 4,410,515 discloses the following compounds having Formula (III) which are active in maintaining calcium and phosphorus metabolism and are useful for treating hypocalcemia in animals:

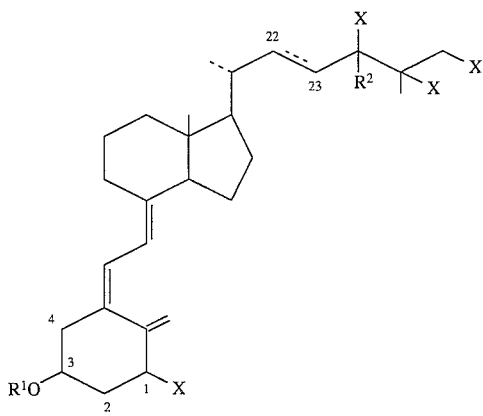

(III)

wherein the bond between positions C-22 and C-23 is single or double; $R^2$ is hydrogen, $CH_3$ or $CH_2CH_3$; X is selected from the group consisting of hydrogen and $-OR^1$, where $R^1$ is hydrogen or a straight or branched chain glycosidic residue containing 1-20 glycosidic units per residue; with the proviso that at least one of the $R^1$ is glycosidic residue.

Fujimoro, et al. (Fujimoro et al., *Experientia* 42:567-568 (1988)) reported the biochemical synthesis of 17β-estradiol-3-(β-D-glucoside) and 17-(α-D-glucoside) by incubation of 17β-estradiol with ovarian tissues from a silkworm. Similarly, incubation of 17α-estradiol 3-glucuronide with rabbit liver microsomes in the presence of uridine diphosphate glucose results in the synthesis of 17α-estradiol-17-(β-glucoside). (Williamson et al., *Biochemistry* 8:45299-4304 (1969)). When 17β-estradiol-17-glucoside and 17α-estradiol-17-glucoside were injected into normal women, the 3-glucuronide derivatives of each compound were recovered in the urine (Williamson et al., *Canadian J. Biochemistry* 50:958-962 (1972)).

SUMMARY OF THE INVENTION

The present invention relates to a method for treating or preventing osteoporosis, as well as a method for alleviating the symptoms of menopause, in an animal having osteoporosis or susceptible to osteoporosis, or undergoing or having undergone menopause, comprising administering to the animal an effective amount of a compound having the Formula (IV):

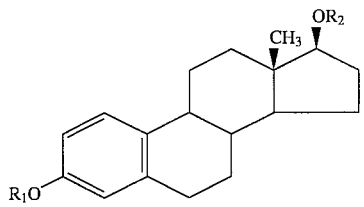

(IV)

wherein $R_1$ and $R_2$ are independently hydrogen or a straight or branched chain glycosidic residue containing 1-20 glycosidic units per residue, or $R_1$ or $R_2$ is an orthoester glycoside moiety of the Formula (V):

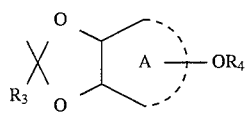

(V)

wherein A represents a glycofuranosyl or glycopyranosyl ring;

$R_3$ is hydrogen, lower alkyl ($C_1$-$C_4$), aralkyl ($C_7$-$C_{10}$), or aryl, with the proviso that aryl is phenyl or phenyl substituted by chloro, fluoro, bromo, iodo, lower $C_1$-$C_4$ alkyl, $C_1$-$C_4$ alkoxy; or naphthyl;

$R_4$ is hydrogen or a straight or branched chain glycosidic residue containing 1-20 glycosidic units per residue;

with the further proviso that at least one of $R_1$ and $R_2$ is either a glycosidic residue or an orthoester glycoside moiety.

DESCRIPTION OF THE PREFERRED EMBODIMENTS

Figure 1A:
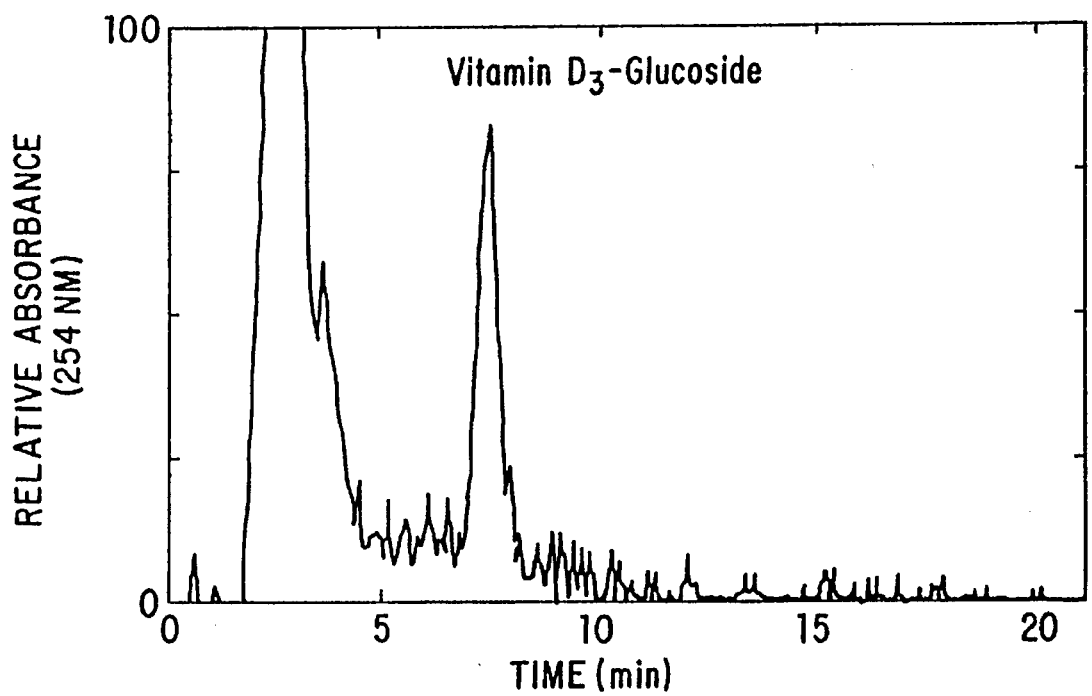
FIG. 1A and FIG. 1B depict reverse phase HPLC (2% $H_2O$/methanol, 1.5 ml/min) of $^3H$-vitamin $D_3$-glucoside before (FIG. 1A) and after (FIG. 1B) incubation with rat intestinal homogenate for 3 hours at 37° C. No $^3H$-vitamin $D_3$ was formed.

The invention is related to the discovery that compounds having Formula (IV) are useful in treating and preventing osteoporosis, as well as in alleviating the symptoms associated with menopause:

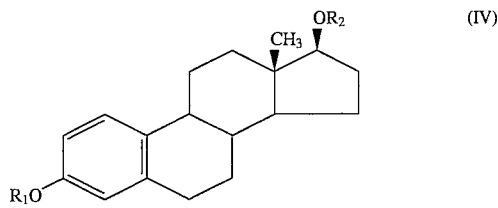

(IV)

wherein $R_1$ and $R_2$ are independently hydrogen or a straight or branched chain glycosidic residue containing 1-20 glycosidic units per residue, or $R_1$ or $R_2$ is an orthoester glycoside moiety of the Formula (V):

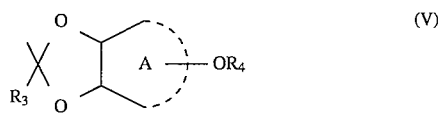

(V)

wherein A represents a glycofuranosyl or glycopyranosyl ring;

$R_3$ is hydrogen, lower alkyl ($C_1$-$C_4$), aralkyl ($C_7$-$C_{10}$), or aryl, with the proviso that aryl is phenyl or phenyl substituted by chloro, fluoro, bromo, iodo, lower $C_1$-$C_4$ alkyl, $C_1$-$C_4$ alkoxy; or naphthyl;

$R_4$ is hydrogen or a straight or branched chain glycosidic residue containing 1-20 glycosidic units per residue;

with the further proviso that at least one of $R_1$ and $R_2$ is either a glycosidic residue or an orthoester glycoside moiety.

According to the invention, the symptoms of menopause which may be alleviated include atrophy of the urogenital epithelium and skin, decreased breast size, hot flashes and osteoporosis. Any animal which experiences any of these symptoms and which may benefit from the estradiol glycosides and orthoester glycosides of Formula IV may be treated according to the present invention. Preferred animals are of course humans, in particular, pre- or post-menopausal women. When administered to a pre-menopausal woman, it is possible to prevent osteoporosis. When administered to a post-menopausal woman, it is possible to reverse the adverse consequences of osteoporosis mentioned above, and arrest the further deterioration of the bones. Administration of these compounds during menopause can alleviate the occurrence of hot flashes, decreased breast size and atrophy of the urogenital tract and skin.

By glycosidic units are meant glycopyranosyl or glycofuranosyl, as well as their amino sugar derivatives. The residues may be homopolymers, random or alternating or block copolymers thereof. The glycosidic units have free hydroxy groups, or hydroxy groups acylated with a group $R_5$—(C=O)—, wherein $R_5$ is hydrogen, lower $C_{1-6}$ alkyl, $C_{6-10}$ substituted or unsubstituted aryl or $C_{7-16}$ aralkyl. Preferably, the acyl groups are acetyl or propionyl. Other preferred groups are where $R_5$ is phenyl, nitrophenyl, halophenyl, lower alkyl substituted phenyl, lower alkoxy substituted phenyl, and the like or benzyl, lower alkoxy substituted benzyl and the like.

The compounds useful in the practice of the invention contain at least one glycoside or orthoester glycoside residue at positions 3 or 17. They may contain, however, two glycoside or orthoester glycoside residues simultaneously.

The glycosides can comprise up to 20 glycosidic units. Preferred, however, are those having less than 10, most preferred, those having 3 or less than 3 glycosidic units. Specific examples are those containing 1 or 2 glycosidic units in the glycoside residue.

The glycopyranose or glycofuranose rings or amino derivatives thereof may be fully or partially acylated or completely deacylated. The completely or partially acylated glycosides are useful as defined intermediates for the synthesis of the deacylated materials.

Among the possible glycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

When more than one glycosidic unit is present on a single hydroxy group (i.e., di or polyglycosidic residues), the individual glycosidic rings may be bonded by 1-1, 1-2, 1-3, 1-4, 1-5 or 1-6 bonds, most preferably 1-2, 1-4 and 1-6. The linkages between individual glycosidic rings may be α or β.

The water soluble glycosidic derivatives of the aforementioned compounds may be obtained according to the general methods set disclosed in Holick, U.S. Pat. No. 4,410,515, the contents of which are fully incorporated by reference herein. The estradiol glycosyl orthoester compounds may be obtained according to U.S. Pat. No. 4,521,410, the contents of which are fully incorporated by reference herein. Preferred estradiol glycosyl orthoesters are 3-estradiol-17β-(α-D-glucopyranosyl-1',2'-orthoacetate) and 17β-estradiol-3-β-glucopyranosyl-1',2'-orthoacetate.

The compounds of the invention can be administered in any appropriate pharmaceutically acceptable carrier for oral, parenteral, or topical administration. They can be administered by any means that treats or prevents osteoporosis or alleviates the symptoms of menopause in animals, especially humans. The dosage administered will be dependent upon the age, health and weight of the recipient, kind of concurrent treatment, if any, frequency of treatment and the nature of the effect desired. For example, systemic daily dosage of 3-(β-glucopyranosyl)-17β-estradiol is from about 0.001 milligrams/kg to 100 milligrams/kg, preferably 0.01 to 1.0 milligrams per kg of body weight. Normally, from about 0.01 to 0.1 milligrams/kg per day of the glycoside or orthoester glycoside, in one or more dosages per day is effective to obtain the desired results. One of ordinary skill in the art can determine the optimal dosages and concentrations of other active estradiol, vitamin D glycoside and orthoester glycoside compounds with only routine experimentation.

The compounds can be employed in dosage forms such as tablets, capsules or powder packets, or liquid solutions, suspensions or elixirs for oral administration, as well as sterile liquid for formulations such as solutions or suspensions for parenteral use. The compounds could also be administered via topical patches, ointments, gels or other transdermal applications. In such compositions, the active ingredient will ordinarily be present in an amount of at least 1.0% by weight based upon the total weight of the composition, and not more than 90% by weight. An inert pharmaceutically acceptable carrier is preferably used. Among such carriers include 95% ethanol, vegetable oils, propylene glycols, saline buffers, etc.

It is well recognized that β-glucosidases do not exist in the small intestine because, if they did, humans would be able to digest cellulose as do ruminants. A study was conducted whereby $^3$H-vitamin $D_3$-3β-glucoside was incubated with intestine and kidney homogenates. It was found that only the kidney homogenate was capable of removing the glucoside from vitamin $D_3$. None of the vitamin $D_3$-3β-glucoside was metabolized in the intestinal homogenates. See FIG. 1. Therefore, the same results for estradiol-3β-glucoside would be expected since vitamin D and estradiol are both fat soluble sterols.

Since the small intestine does not contain β-glucosidases, it would not be expected that the liver would receive free estradiol coming from the intestine after the oral ingestion of estradiol-3-(β-glucoside). Thus, this would lessen the first pass effect of estradiol-3-(β-glucoside) when compared to estradiol itself.

Figure 1B:
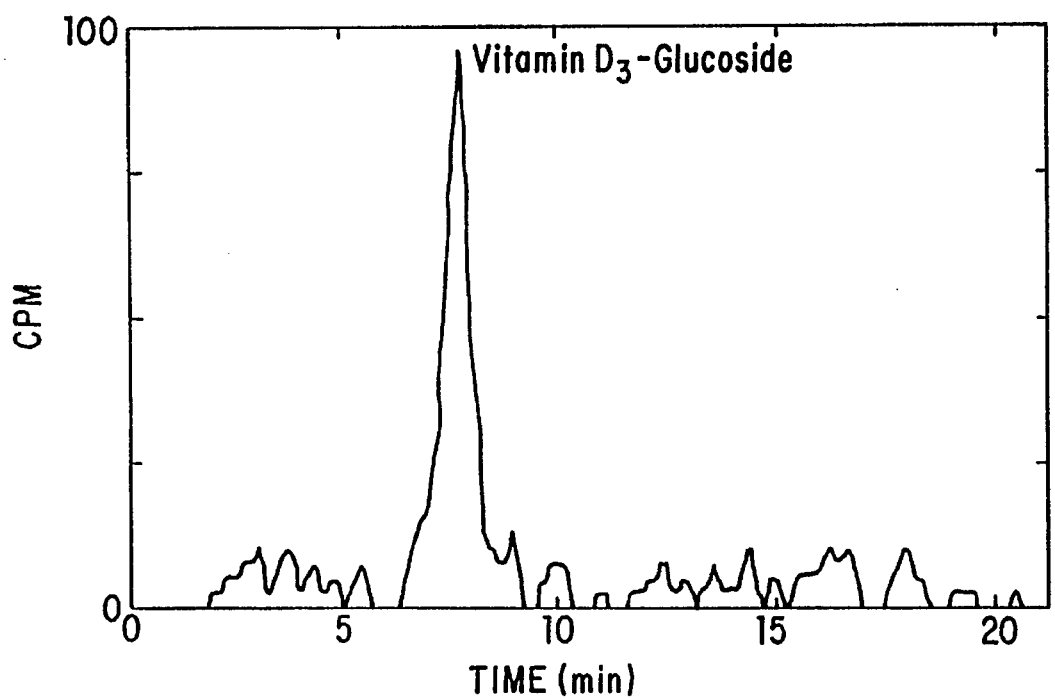
Figure 1C:
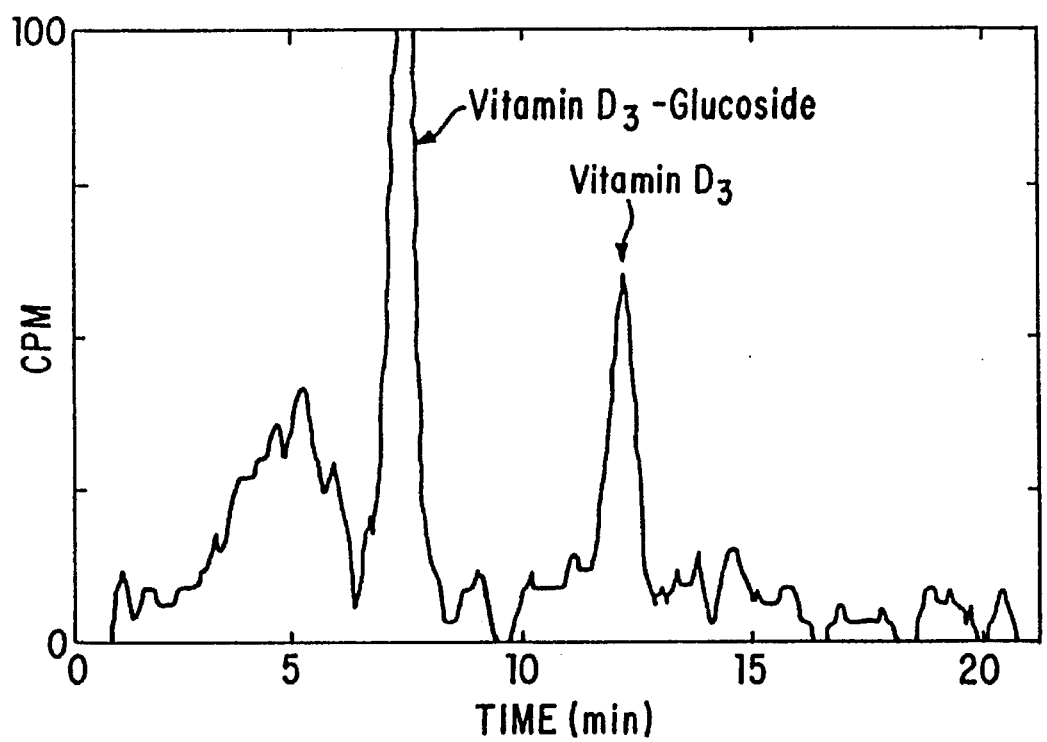
FIG. 1C depicts reverse phase HPLC (2% $H_2O$/methanol, 1.5 ml/min) of $^3H$-vitamin $D_3$-glucoside after incubation with rat kidney homogenate for 3 hours at 37° C. Note the formation of $^3H$-vitamin $D_3$.

In vivo rat studies have shown that when estradiol-3-(β-glucoside) was given orally for two weeks to ovariectomized rats, estradiol was found in the circulation (Table 1). Thus, the non-specific β-glucosidases found in peripheral tissues appear to be responsible for the de-conjugation of estradiol-3-(β-glucoside) to estradiol. As shown in FIG. 1, a study with the vitamin D-3β-glucoside as a model compound was conducted which shows that β-glucosidase(s) in the kidney are able to de-conjugate the β-glucoside from the vitamin D-3β-glucoside.

One of the potential side-effects of giving estradiol orally is its first pass biologic effect on the liver especially as it relates to increasing the synthesis of proteins associated with blood clotting. Since there is evidence that estradiol-3-(β-glucoside) does not interact with the estradiol receptor, it would be expected that the estradiol-3-(β-glucoside) would not have the same potency of activity in increasing blood clotting factors in the liver as estradiol itself.

Figure 2A:
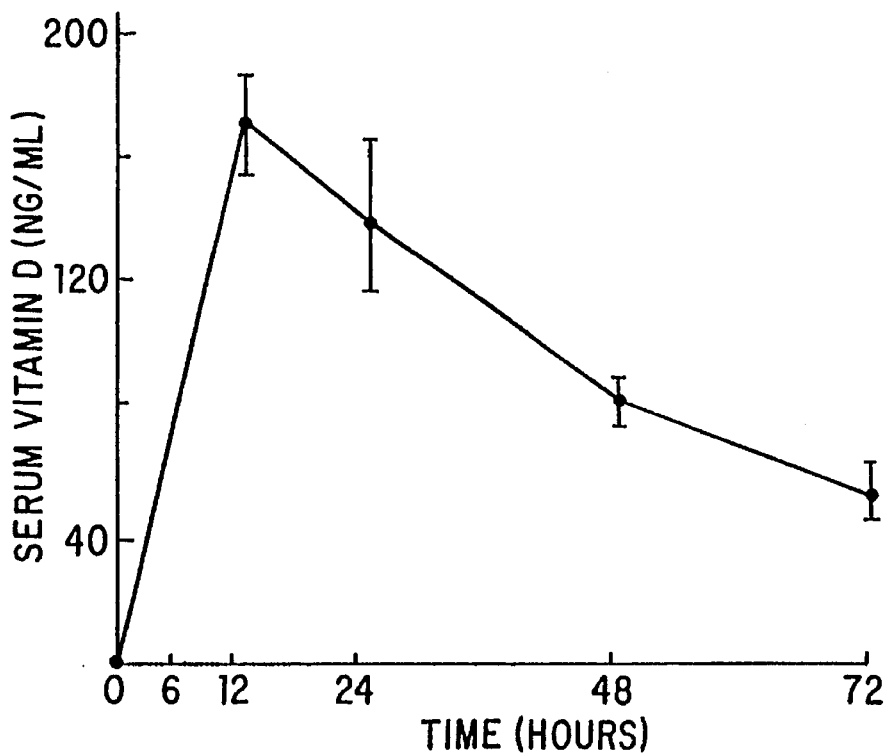
FIG. 2A and FIG. 2B depict serum vitamin D concentration versus time in normal human subjects that have been orally administered 3250 nmoles of vitamin $D_3$ (FIG. 2A) or vitamin $D_3$-glucoside (FIG. 2B).
Figure 2B:
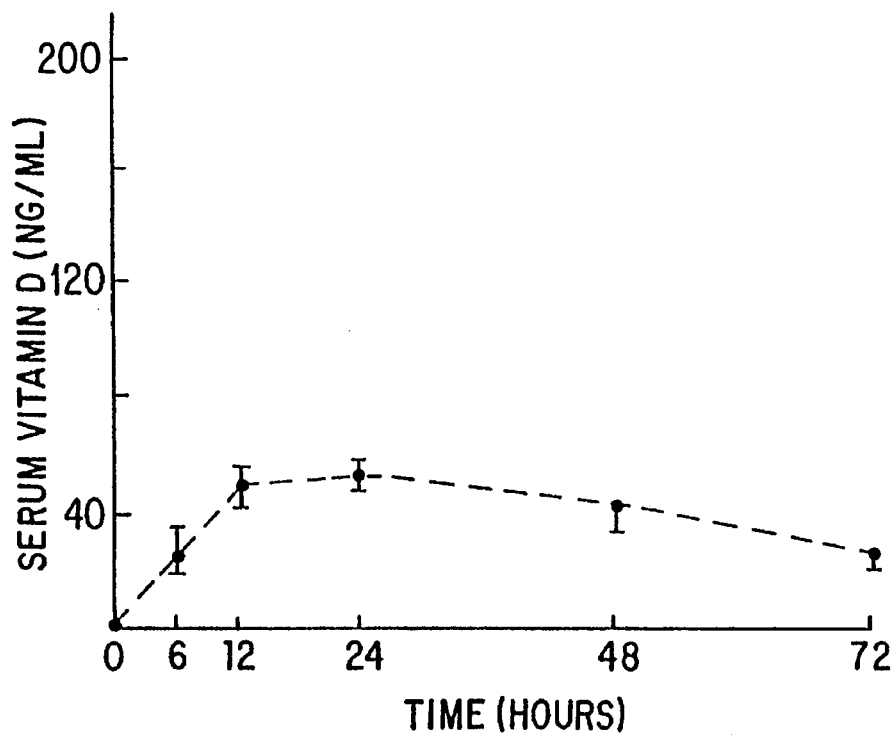

De-conjugation of estradiol-3-(β-glucoside) to estradiol will occur slowly in peripheral tissues, and therefore, will maintain circulating levels of estradiol at a more physiologic level for a longer period of time. A study in humans with the vitamin D-3β-glucoside was conducted as a model compound. The blood level of vitamin D after an equimolar dose of vitamin $D_3$ and vitamin $D_3$-3β-glucoside was compared. As can be seen in FIG. 2, the blood levels of vitamin $D_3$ resulting from the de-conjugation of its glucoside is about 30% of that achieved when the same dose of vitamin $D_3$ was given orally. Thus, from this single dose vitamin D-glucoside study, there would not appear to be any hazard to the prolonged duration of action of the estradiol resulting from the slow de-conjugation of the estradiol-3-(β-glucoside). A study in ovariectomized rats was also conducted to determine the blood level of estradiol and estrone after receiving three different doses of either estradiol or estradiol-3-(β-glucoside) orally each day for two weeks. As can been seen in Table 1, the circulating estradiol levels in the rats receiving either 1, 10 or 15 nmol of estradiol-3-(β-glucoside) were comparable or lower to the rats receiving the same doses of estradiol. Thus, estradiol-3-(β-glucoside) will increase circulating concentrations of estradiol.

Based on the results in rats and humans with the model vitamin D-3β-glucoside and experience with giving estradiol-3-(β-glucoside) to ovariectomized rats, there is no indication of potential additive or multiplicative toxicity. Indeed, in the study where oral administration of estradiol-3-(β-glucoside) to ovariectomized rats was evaluated for a period of two weeks, it was found that the β-estradiol levels were either no different or lower compared to the animals that received unconjugated estradiol (Table 1). No untoward side-effects or vaginal bleeding was noted in either group of rats.

Having now generally described this invention, the same will be understood by reference to the following examples which are provided herein for purposes of illustration only and are not intended to be limiting unless otherwise specified.

EXAMPLE 1

The synthesis of 17β-estradiol-3-(β-glucoside)

Figure 3:
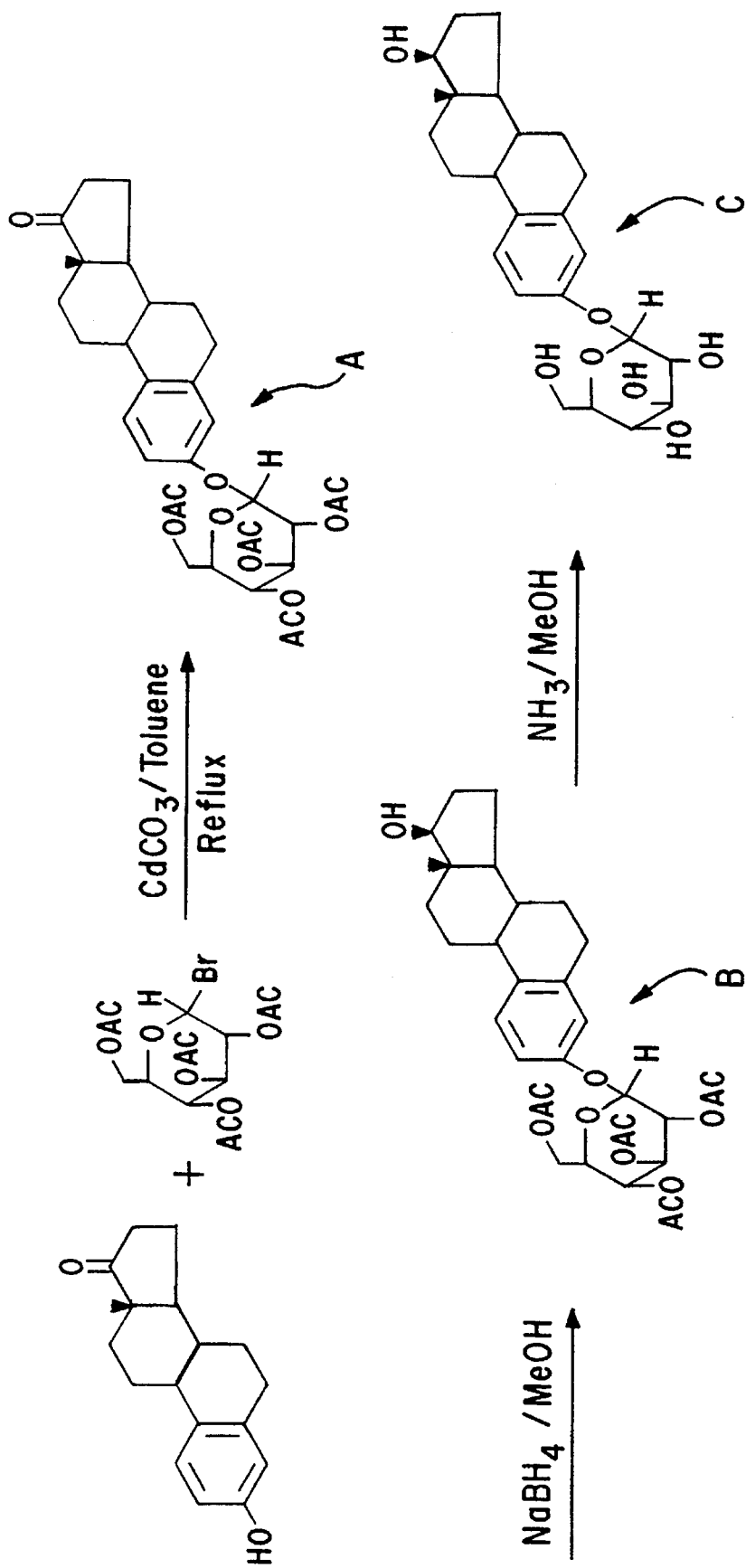
FIG. 3 illustrates a synthetic scheme for preparing 17B-estradiol-3B-glucoside.

17β-Estradiol-3-β-glucoside was synthesized as outlined in FIG. 3. Estrone was coupled with acetobromoglucose in the presence of cadmium carbonate ($CdCO_3$) as a catalyst following the procedure of Conrow and Bernstein (Conrow and Bernstein, *J. Org. Chem.* 36:863–870 (1971)). The estrone 3β-2'3',4',6'-tetra-O-acetyl-D-glucopyranoside (A) was the predominant product (>60%) of the reaction and was obtained by crystallization. The melting point of the product was 212°–214° C. (reported mp 212°–216° C.) (Conrow and Bernstein, *J. Org. Chem.* 36:863–870 (1971)). The IR and NMR spectra of this product matched that of reported values (Conrow and Bernstein, *J. Org. Chem.* 36:863–870 (1971)).

The estrone conjugate (A) was reduced with sodium borohydride at 0° C. in methanol-THF. This reduction resulted in the stereo specific formation of the 17β-alcohol (Hobkirk et al., *J. Clin. Endocrinol.* 32:476–480 (1971)). The product (B) was obtained in almost quantitative yield after preparative TLC purification from silica plates (2:1 hexane-ethyl acetate).

Compound B was treated with methanolic ammonia at 4° C. Removal of the solvent and trituration with water produced a white crystalline solid, mp 210°–220° C. The yield of the product (C), 17β-estradiol-3β-glucoside was quantitative. The HPLC analysis of the product ($C_{18}$-column, 20% water in methanol, 0.5 ml/minute, monitored with a UV detector set at 254 nm) produced a single peak which demonstrated its homogeneity. Interpretation of NMR and mass spectrum data is given below.

EXAMPLE 2

Physico-Chemical Analysis of 17β-Estradiol-3β-Glucoside (C)

The UV absorption spectrum for compound C in methanol had a typical spectrum for estradiol, wherein $\lambda_{max}$=280 nm.

For the mass spectrum and NMR analysis of compound C, it was converted to its penta-O-acetyl derivative by treatment with pyridine-acetic anhydride-catalytic amount of 4,4'dimethylaminopyridine. The reaction product was homogeneous on TLC and was purified by HPLC on a silica column with 5% isopropanol in n-hexane at 1 ml/minute. The isolated compound was analyzed by FABMS and NMR:

FABMS: 662.6, 643.5, 332.3, 331.3, 288.4.

NMR: (200 MHz; $CDCl_3$ solvent, TMS internal standard) δ7.28 (overlapped with 7.26 peak of $CHCl_3$, aromatic H); δ6.85 (m, aromatic H, 2H), δ5.15 (m, 4H, H–1', 2', 3', 4'), δ4.56 (d, J=9 Hz; 1H, 17-CH); δ4.2 (m, 2H, 6'-$CH_2$), δ3.72 (m, 1H, 5'-CH); δ2.85 (m, 2H, H-6-$CH_2$); δ2.3 and 2.2 (5 singlets, 15 H, 5-OAc-protons); δ0.75 (s, 3H, 18-$CH_3$).

EXAMPLE 3

In vivo Rat Studies

In vivo rat studies were carried out where estradiol-3-(β-glucoside) was given orally for two weeks to ovariectomized rats. Estradiol was detected in the circulation by radioimmunoassay, using a kit purchased from ICN Biomedical (Costa Mesa Calif., 92626). The results are shown in Table 1.

TABLE 1

Circulating concentration of 17β-estradiol and estrone in six ovariectomized rats per group that received an oral dose of either 17β-estradiol or 17β-estradiol-3 β-glucoside (estradiol-glc) each day for two weeks.

| Compounds | Dose (mmol) | Blood Concentrations Estradiol | (pg/ml) Estrone |
|---|---|---|---|
| 1. control | 0 | 3.2 ± 0.5 | 22.7 ± 3.6 |
| 2. estradiol | 1 | 3.5 ± 0.7 | 17.8 ± 2.0 |
| 3. estradiol | 10 | 8.7 ± 2.1 | 18.5 ± 2.9 |
| 4. estradiol | 15 | 46.8 ± 10.4 | 19.8 ± 7.0 |
| 5. estradiol-glc | 1 | 3.8 ± 0.7 | 12.2 ± 1.5 |
| 6. estradiol-glc | 10 | 7.7 ± 2.1 | 12.8 ± 1.5 |
| 7. estradiol-glc | 15 | 12.3 ± 3.4 | 11.5 ± 0.7 |

As can been seen in Table 1, the circulating estradiol levels in the rats receiving either 1, 10 or 15 nmol of estradiol-3-(β-glucoside) were comparable or lower to the rats receiving the same doses of estradiol.

From the foregoing description, one skilled in the art can easily ascertain the essential characteristics of this invention, and without departing from the spirit and scope thereof, can make various changes and modifications of the invention to adapt it to various usages and conditions without undue experimentation. All patents and publications cited herein are incorporated by reference in their entirety.

What is claimed is:

1. A method for treating or preventing osteoporosis in an individual in need thereof, comprising administering to said individual an effective amount of a compound having the formula:

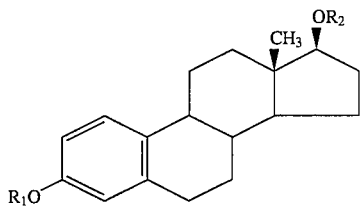

wherein $R_1$ and $R_2$ are independently hydrogen or a straight or branched chain glycosidic residue containing 1–20 glycosidic units per residue, or $R_1$ or $R_2$ is an orthoester glycoside moiety of the formula:

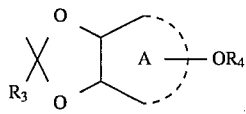

wherein A represents a glycofuranosyl or glycopyranosyl ring; with the further proviso that at least one of $R_1$ and $R_2$ is either a glycosidic residue or an orthoester glycoside moiety;

$R_3$ is hydrogen, lower alkyl ($C_1$-$C_4$), aralkyl ($C_7$-$C_{10}$), phenyl or phenyl substituted by chloro, fluoro, bromo, iodo, lower $C_1$-$C_4$ alkyl, $C_1$-$C_4$ alkoxy; or naphthyl; and $R_4$ is hydrogen or a straight or branched chain glycosidic residue containing 1–20 glycosidic units per residue.

2. A method for alleviating the symptoms of menopause in an individual undergoing or having undergone menopause, comprising administering to said individual an effective amount of a compound having the formula:

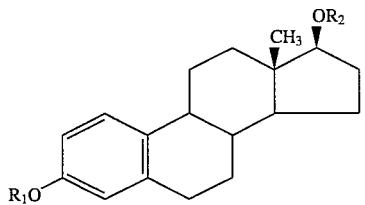

wherein $R_1$ and $R_2$ are independently hydrogen or a straight or branched chain glycosidic residue containing 1–20 glycosidic units per residue, or $R_1$ or $R_2$ is an orthoester glycoside moiety of the formula:

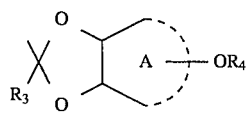

wherein A represents a glycofuranosyl or glycopyranosyl ring; with the further proviso that at least one of $R_1$ and $R_2$ is either a glycosidic residue or an orthoester glycoside moiety;

$R_3$ is hydrogen, lower alkyl ($C_1$-$C_4$), aralkyl ($C_7$-$C_{10}$), phenyl or phenyl substituted by chloro, bromo, iodo, lower $C_1$-$C_4$ alkyl, $C_1$-$C_4$ alkoxy; or naphthyl; and $R_4$ is hydrogen or a straight or branched chain glycosidic residue containing 1–20 glycosidic units per residue.

3. The method of claim 1 or 2, wherein said compound is 17β-estradiol-3-(β-glucoside).

4. The method of claim 1 or 2, wherein said compound is administered in an amount ranging from about 0.01 to 10 milligrams/kg per day.

5. The method of claim 1 or 2, wherein said compound is administered as part of a pharmaceutical composition comprising a pharmaceutically acceptable carrier.

6. The method of claim 1, wherein said individual is suffering from or has suffered from menopause.

7. The method of claim 1 or 2, wherein said compound is administered to a woman prior to the onset of menopause.

8. A compound having the formula:

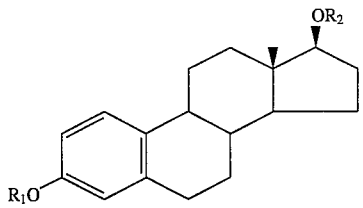

wherein $R_1$ is hydrogen, a straight or branched chain glycosidic residue containing 1–20 glycosidic units per residue, or an orthoester glycoside moiety of the formula:

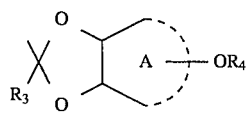

wherein A represents a glycofuranosyl or glycopyranosyl ring;

$R_2$ is an orthoester glycoside residue having the above formula, or a hydrogen when $R_1$ is an orthoester glycoside moiety;

$R_3$ is hydrogen, lower alkyl ($C_1$-$C_4$), aralkyl ($C_7$-$C_{10}$), phenyl or phenyl substituted by chloro, fluoro, bromo, iodo, lower $C_1$-$C_4$ alkyl, $C_1$-$C_4$ alkoxy; or naphthyl; and $R_4$ is hydrogen or a straight or branched chain glycosidic residue containing 1–20 glycosidic units per residue.

9. The compound of claim 8 which is 3-estradiol-17β-(α-D-glucopyranosyl-1',2'-orthoacetate).

10. The compound of claim is 17β-estradiol-3-β-glucopyranosyl-1',2'-orthoacetate.

* * * * *